United States Patent [19]

Polacin et al.

[11] Patent Number: 5,604,778
[45] Date of Patent: Feb. 18, 1997

[54] SPIRAL SCAN COMPUTED TOMOGRAPHY APPARATUS WITH MULTIPLE X-RAY SOURCES

[75] Inventors: Arkadiusz Polacin; Christoph Suess, both of Erlangen, Germany

[73] Assignee: Siemens Aktiengesellschaft, Munich, Germany

[21] Appl. No.: 541,175

[22] Filed: Oct. 11, 1995

[30] Foreign Application Priority Data

Oct. 13, 1994 [DE] Germany .......................... 44 36 688.4

[51] Int. Cl.⁶ .................................................. A61B 6/03
[52] U.S. Cl. .................................................. 378/9; 378/15
[58] Field of Search ................................. 378/9, 15, 4, 19

[56] References Cited

U.S. PATENT DOCUMENTS

| | | | |
|---|---|---|---|
| 4,150,293 | 4/1979 | Franke | 250/445 |
| 4,384,359 | 5/1983 | Franke . | |
| 5,068,882 | 11/1991 | Eberhard | 378/9 X |
| 5,291,402 | 3/1994 | Pfoh . | |
| 5,375,156 | 12/1994 | Kuo-Petravic et al. | 378/9 |
| 5,430,783 | 7/1995 | Hu et al. | 378/15 |
| 5,454,019 | 9/1995 | Migita et al. | 378/15 |

FOREIGN PATENT DOCUMENTS

| | | | |
|---|---|---|---|
| 2729833 | 1/1979 | Germany . | |
| 2020138 | 11/1979 | United Kingdom | 378/9 |

*Primary Examiner*—David P. Porta
*Attorney, Agent, or Firm*—Hill, Steadman & Simpson

[57] ABSTRACT

A spiral scan computed tomography apparatus has multiple x-ray sources with their respective foci symmetrically arranged on a circle concentric with a measurement field around which the x-ray sources are rotated in order to spirally scan an examination subject while a relative motion between the x-ray sources and a patient support is produced along a longitudinal direction of the patient support. X-rays attenuated by the examination subject are detected by a stationary detector ring, or by a number of detector arrays which co-rotate with the x-ray sources on the gantry. The scan time can thereby be decreased in comparison to known systems or, within the same scan time a higher x-ray power can be achieved.

7 Claims, 2 Drawing Sheets

SPIRAL SCAN COMPUTED TOMOGRAPHY APPARATUS WITH MULTIPLE X-RAY SOURCES

BACKGROUND OF THE INVENTION

1. Field of the Invention

The present invention is directed to a computed tomography apparatus of the type for conducting a spiral scan (sometimes referred to as a spiral-helical scan) of an examination volume.

2. Description of the Prior Art

The technique of spiral scanning of a volume is acquiring increasing significance in the field of computed tomography. For this purpose, an exposure unit, composed of an x-ray source (x-radiator) and a radiation detector are mounted on a gantry or scan-frame, and the gantry or frame is rotated through an angle larger than 360° while the patient support is moved in a longitudinal direction through the scanned measurement field. Such a spiral scan computed tomography apparatus is disclosed, for example, in the U.S. Pat. No. 5,291,402.

SUMMARY OF THE INVENTION

It is the object of the present invention to provide a spiral scan tomography apparatus wherein an examination volume can be spirally scanned with a higher x-ray power, thereby resulting in a shorter exposure time in comparison to known spiral scan tomography systems.

The above object is achieved in accordance with the principals of the present invention in a spiral scan computed tomography apparatus for scanning an examination volume, having a plurality of x-ray sources (x-radiators) each having a focus, with the foci of the x-ray sources being symmetrically disposed on a circle which is concentric with the measurement field. The x-ray sources are continuously rotatable around a system axis, while a relative motion ensues between the x-ray sources and the patient support along the longitudinal direction of the patient support.

X-rays attenuated by a subject in the examination field are detected by an x-ray detector ring, which may be stationary, or a number of detector arrays can be used, which co-rotate around the system axis with the x-ray sources. Regardless of whether a stationary detector ring or a number of co-rotating detector arrays are used, each ring or ray may be composed of a number of rows of detector elements.

DESCRIPTION OF THE PREFERRED EMBODIMENTS

Figure 1:
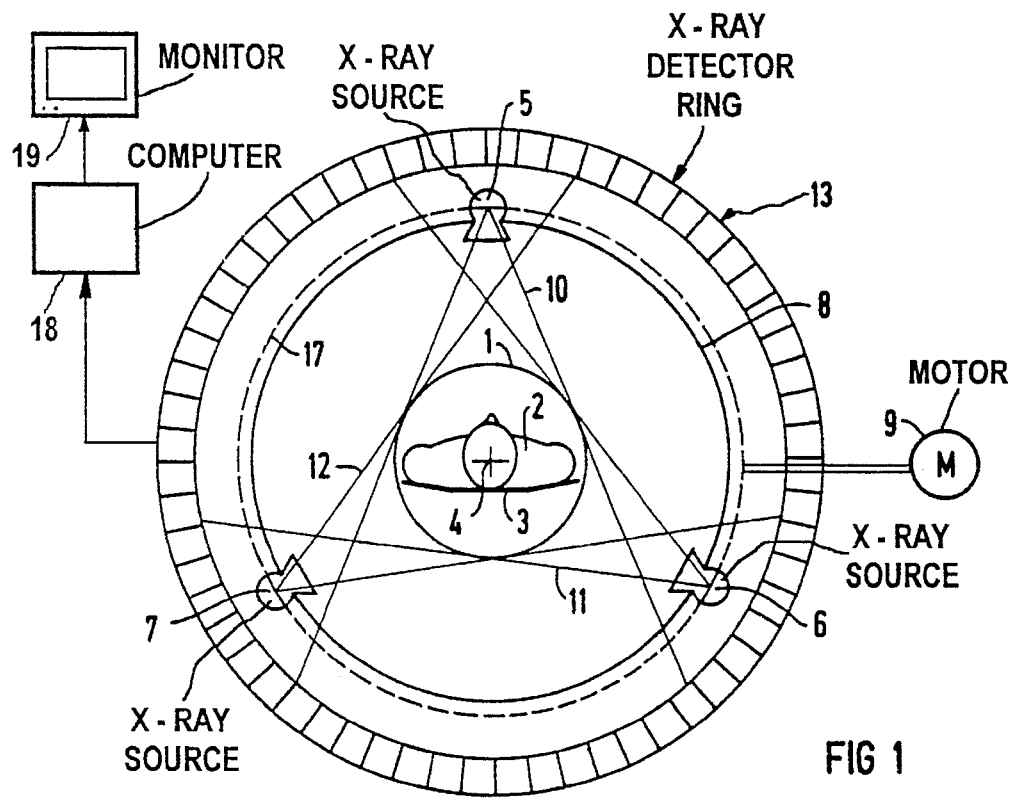
FIG. 1 is a schematic illustration of a spiral scan computed tomography apparatus constructed in accordance with the principals of the present invention, seen in an end view.

The spiral scan computed tomography apparatus shown in FIG. 1 has a measurement field 1 in which is a patient 2 is disposed lying on a patient support 3. For producing tomograms through a system axis 4 proceeding perpendicularly to the plane of the drawing, the patient 2 is scanned by multiple, such as 3, x-ray sources (x-radiators) 5, 6, and 7. The x-ray sources 5, 6 and 7 are respectively disposed on a gantry 8 with an angle of 120° between neighboring x-ray sources. The gantry 8 is continuously rotated by a motor 9 for conducting a scan. The x-ray sources 5, 6 and 7 emit respective fan-shaped x-ray beams 10, 11 and 12, which penetrate the measurement field 1 and the patient 2 and, attenuated by the patient 2, are incident on a detector ring 13. In the embodiment shown in FIG. 1, the detector ring 13 is stationary. The radiation detector may alternatively be formed by a number of detector arrays which rotate on the gantry 8, with 1 detector array being disposed opposite each x-ray source 5, 6 and 7, so that a total of three detector arrays would be present in the exemplary embodiment of FIG. 1.

Regardless of whether a detector ring or a number of detector arrays are employed, each is composed of one or more rows of detector elements. Each detector element emits an electrical output signal dependent on the x-rays incident thereon, with the output signals of the detector elements being supplied in a known manner to a computer 18 which calculates images of the entire transirradiated region of the patient 2, and reproduces these images on a monitor 19. The patient support 3 is pushed through the measurement field 1 along its longitudinal direction, i.e. parallel to the system axis 4, while the gantry 8 with the x-ray sources 5, 6 and 7 is being rotated, so that a volume of the patient 2 is spirally (helically) scanned.

Figure 2:
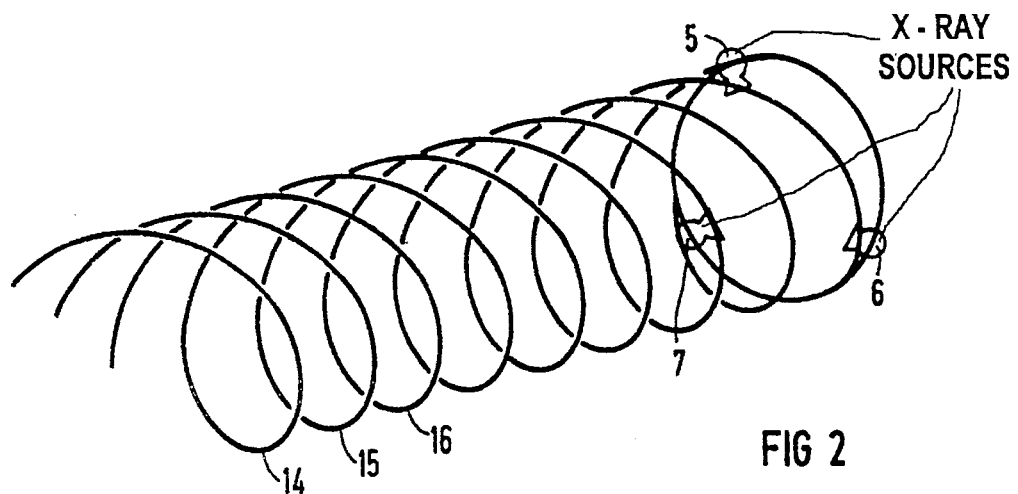
FIG. 2 is a schematic illustration of the scan curves of the respective x-ray sources in the spiral scan computed tomography apparatus of FIG. 1.

Three paths 14, 15 and 16 are shown in FIG. 2, on which the respective foci of the x-ray sources 5, 6 and 7 would move if the patient support 3 were stationary and the gantry 8 were moved along the direction of the system axis 4. The foci are disposed on a circle 17 (see FIG. 1) concentric with the detector ring 13.

The exemplary embodiment shown in FIG. 1 of a spiral computed tomography apparatus having a stationary detector ring 13 and a plurality, namely 3, x-ray sources 5, 6 and 7 on the rotating gantry 8 has the following advantages over known spiral scan tomography systems.

Figure 3:
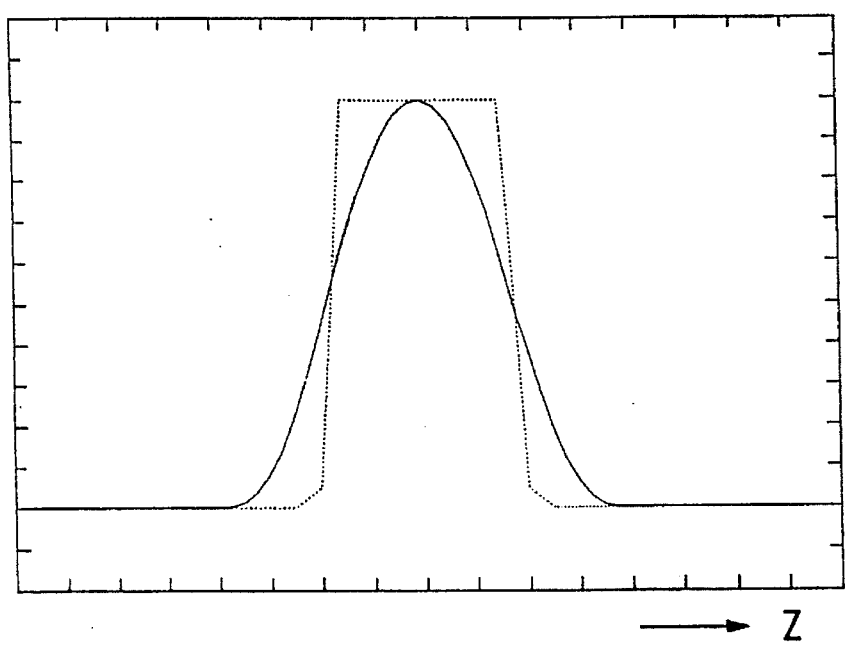
FIG. 3 illustrates a slice profile obtained by conventional spiral scanning.
Figure 4:
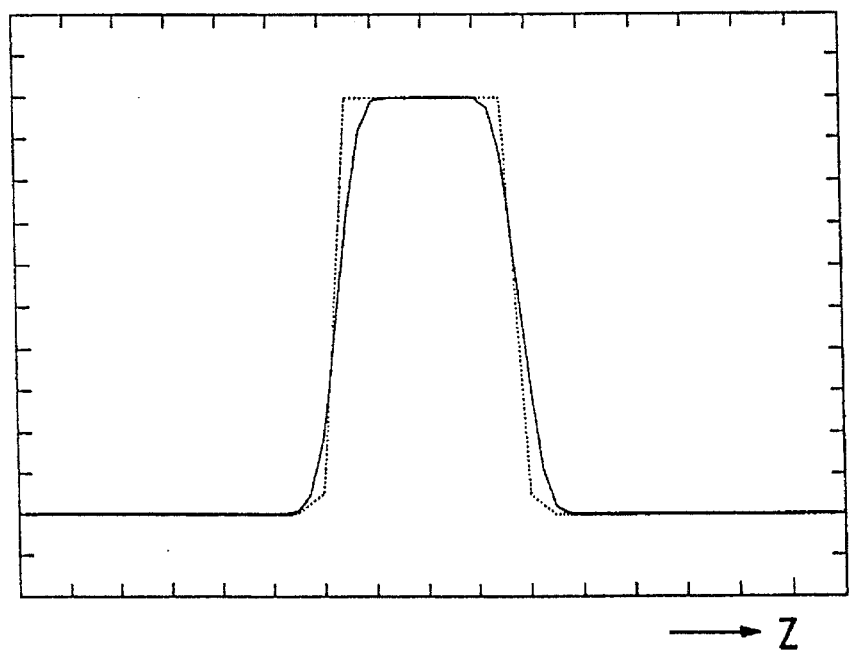
FIG. 4 illustrates a slice profile obtained by scanning according to FIG. 2 using the inventive apparatus of FIG. 1.

First, the use of multiple x-ray sources, preferably 3 x-ray sources, offers a high degree of flexibility. Given a feed of the patient 2 on the patient support 3 by one slice thickness per 360° of revolution (pitch=1), a trebly improved scanning is achieved in forward feed direction and spiral artifacts are thus avoided. Slice profile and quanta of the calculated tomograms can be retroactively varied over a broad range. In the best case, the slice profile is approximately identical to a discrete slice (shown in dashed lines in FIG. 4). By contrast, FIG. 3 shows the large deviation between the measured slice profile and the slice profile of a discrete slice in the case of a conventional spiral scan computed tomography apparatus using only one x-ray source. Slices having a higher number of quanta have a correspondingly broader, but approximately trapezoidal, profile and exhibit fewer sub-volume artifacts than a discrete slice of the same breadth. The finer scanning in the forward feed direction improves the spiral interpolation considerably, and assures a uniform distribution of image noise and spatial resolution in the image plane. The scanning can be improved further by using a plurality of parallel detector rows. The fine scanning of the patient 2 in the forward feed direction also permits an "unfolding" or development of the measured raw data, and can result in a slice sensitivity profile which is better than can be achieved by mechanical collimation of the x-rays. As a result, an approximately uniform distribution of the image resolution is achieved in the three spatial directions.

Secondly, the x-ray power is a multiple of the power achieved in a conventional apparatus (for example, three times the power given employment of three X-ray sources 5, 6 and 7). The x-ray power achieved in accordance with the principals of the present invention is comparable to the effective x-ray power (usable image quanta) of an electron beam machine (EBT) or of a conventional apparatus having a multi-line detector.

Third, the effective measuring time for a frame in the inventive apparatus is only a fraction of the current exposure time, for example ⅓ of 0.5 sec., i.e. 0.17 sec for a 360° data acquisition, and less than 100 msec for a partial scan. These times are quite comparable to the times associated with an electron beam apparatus, and are clearly superior to those of conventional spiral scan systems. Moreover, the scan time can be lengthened as desired and matched to the necessary dose per frame without increasing the quantity of measured data.

The pitch can be increased as needed (thin-slice exposure of large volumes, for example lungs). Given pitch=3, the scanning and image quality of currently available spiral scan systems are achieved in one-third the time or for triple the volume.

The planar exposure geometry employed in the apparatus of the invention avoids cone beam artifacts and, therefore the correspondingly high, additional calculating outlay needed to compensate for these artifacts is also avoided. The cone angle can be selected to be extremely small given the use of the number of detector rows. The image quality of the spiral scan computed tomography system disclosed herein exceeds both that of an electron-beam apparatus as well as that of a conventional, multi-row detector apparatus.

In the embodiment employing a stationary detector ring 13, the same detector ring is simultaneously employed by all of the x-ray sources, thus serving triple duty, and thus, the additional apparatus costs are limited only to two further x-ray sources and the associated increased high voltage generating capacity.

Although modifications and changes may be suggested by those skilled in the art, it is the intention of the inventors to embody within the patent warranted hereon all changes and modifications as reasonably and properly come within the scope of his contribution to the art.

We claim as our invention:

1. A spiral scan computed tomography apparatus comprising:

a gantry rotatable around a system axis extending through a measurement field;

a plurality of x-ray sources disposed on said gantry and co-rotatable therewith, each x-ray source having a focus and the respective foci of said x-ray sources being symmetrically disposed on a circle concentric with said measurement field;

support means for supporting an examination subject, said support means having a longitudinal access extending substantially parallel to said system axis;

means for producing relative motion along said longitudinal axis of said support means between said support means and said x-ray sources while said x-ray sources are rotated around said measurement field on said gantry for spirally scanning a subject on said support means with x-rays from said x-ray sources;

radiation detector means for detecting radiation attenuated by said subject while said subject is spirally scanned and for generating electrical signals corresponding thereto; and computer means for generating a tomographic image of said subject from said electrical signals.

2. A computed tomography apparatus as claimed in claim 1 wherein said plurality of x-ray sources comprises three x-ray sources.

3. A computed tomography apparatus as claimed in claim 1 wherein said means for detecting comprises a stationary detector ring surrounding said measurement field.

4. A computed tomography apparatus as claimed in claim 3 wherein said stationary detector ring comprises a plurality of rows of detector elements.

5. A computed tomography apparatus as claimed in claim 1 wherein said means for detecting comprises a plurality of radiation detector arrays respectively disposed opposite said plurality of x-ray sources, said plurality of detector arrays being mounted on said gantry for co-rotation with said plurality of x-ray sources.

6. A computed tomography apparatus as claimed in claim 5 wherein each detector array comprises a plurality of rows of detector elements.

7. A method for obtaining a computed tomogram of a subject comprising:

symmetrically disposing a plurality of x-ray sources around a measurement field, each x-ray source having a focus and the respective foci of said x-ray sources being disposed on a circle concentric with said measurement field;

placing a subject on a support having a longitudinal axis;

rotating said plurality of x-ray sources around said subject on said support while producing a relative motion along said longitudinal axis between said x-ray sources and said support and thereby conducting a spiral scan of said subject with x-rays emitted by said plurality of x-ray sources;

detecting x-rays attenuated by said subject during the spiral scan of said subject and generating electrical signals corresponding to the attenuated x-rays; and generating a tomographic image of said subject from said electrical signals.

* * * * *